United States Patent [19]

Badylak et al.

[11] Patent Number: 5,753,267
[45] Date of Patent: May 19, 1998

[54] METHOD FOR ENHANCING FUNCTIONAL PROPERTIES OF SUBMUCOSAL TISSUE GRAFT CONSTRUCTS

[75] Inventors: Stephen F. Badylak, W. Lafayette; Sherry Voytik, Lafayette, both of Ind.

[73] Assignee: Purdue Research Foundation, West Lafayette, Ind.

[21] Appl. No.: 530,001

[22] Filed: Sep. 19, 1995

Related U.S. Application Data

[62] Division of Ser. No. 386,452, Feb. 10, 1995, Pat. No. 5,695,998.
[51] Int. Cl.$^6$ .............................. A61K 35/38; C12N 5/00; C12N 5/08; A61F 2/08
[52] U.S. Cl. .................... 424/551; 424/93.1; 435/325; 435/366; 435/371; 435/377; 435/402; 623/15
[58] Field of Search ..................... 435/325, 366, 435/371, 377, 402; 424/93.1, 551; 623/15

[56] References Cited

U.S. PATENT DOCUMENTS

| | | | |
|---|---|---|---|
| 4,439,521 | 3/1984 | Archer et al. | 435/240.23 |
| 4,743,552 | 5/1988 | Friedman et al. | 435/240.23 |
| 4,829,000 | 5/1989 | Kleinman et al. | 435/240.23 |
| 4,902,508 | 2/1990 | Badylak et al. | 424/95 |
| 4,958,178 | 9/1990 | Badylak et al. | 424/551 |
| 5,266,480 | 11/1993 | Naughton et al. | 435/240.243 |
| 5,275,828 | 1/1994 | Badylak et al. | 424/551 |
| 5,281,422 | 1/1994 | Badylak et al. | 424/551 |
| 5,352,483 | 10/1994 | Badylak et al. | 424/551 |
| 5,372,821 | 12/1994 | Badylak et al. | 424/551 |
| 5,478,739 | 12/1995 | Slivka et al. | 435/240.23 |
| 5,518,915 | 5/1996 | Naughton et al. | 435/240.23 |

FOREIGN PATENT DOCUMENTS

| | | |
|---|---|---|
| WO 92/15676 | 9/1992 | WIPO. |
| PCT/US92/ 05267 | 1/1993 | WIPO. |

OTHER PUBLICATIONS

Emerman et al., "Maintenance and Induction of Morphological Differentiation in Dissociated Mammary Epithelium on Floating Collagen Membranes", In Vitro, vol. 13, No. 5, pp. 316–328, 1977.

Bell et al., "Production of a tissue-like structure by contraction of collagen lattices by human fibroblasts of different proliferative potential in vitro ", Proc. Natl. Sci. USA, vol. 76, No. 3, pp. 1274–1278, Mar. 1979.

Elsdale et al., "Collagen Substrate for Studies on Cell Behavior", The Journal of Cell Biology, vol. 54, pp. 626–637, 1972.

Kleinman et al., "Preparation of Collagen Substrates for Cell Aattachment: Effect of Collagen Concentration and Phosphate Buffer", Analytical Biochemistry, No. 94, pp. 308–312, 1979.

Vitrogen 100®Purified Collagen for Cell Culture and Biochemistry: Product Information Sheet, pp. 1–2, 1980.

Grinnell, "Cell–Collagen Interactions: Overview", Methods in Enzymology, vol. 82, pp. 499–503, 1982.

Lee et al., "Modulation of Secreted Proteins of Mouse Mammary Epithelial Cells by the Collagenous Substrata", The Journal of Cell Biology, vol. 98, pp. 146–155, 1984.

Schor et al., "The Use of Three–Dimentional Collagen Gels for the Study of Tumor Cell Invasion In Vitro: Experimental Parameters Influencing Cell Migration Into the Gel Matrix", Int. J. Cancer, vol. 29, pp. 57–62, 1982.

Shields et al., "Invasion of Collagen Gels by Mouse Lymphoid Cells", Immunology, vol. 51, pp. 259–268, 1984.

Schor et al., "Effects of Culture Conditions on the Proliferation, Morphology and Migration of Bovine Aortic Endothelial Cells", J. Cell Sci., vol. 62, pp. 267–285, 1983.

Michalopoulos et al., "Primary Culture of Parenchymal Liver Cells on Collagen Membranes", Experimental Cell Research, vol. 94, pp. 70–78, 1975.

Housseiny, El et al., Orthotopic Implantation of Primary N–[4–(5–Nitro–2–furyl)–2–thiazoiyl]formamide–induced Bladder Cancer in Bladder Submucosa: An Animal Model for Bladder Cancer Study, Cancer Research, vol. 43:617–620, Feb. 1983.

Kashtan, H. et al., Intra–rectal injection of tumor cells: a novel animal model of rectal cancer, Surgical Oncology, 1:251–256, 1992.

Sigma 1994 Catalogue and Price List, Plant Cell Culture Equipment, p. 160.

Long–Term Production of Insulin by Isolated Rabbit Pancreatic Islets in Suspension Culture. Boder, G.B., Root, Mary A., Chance, R.E., and Johnson, I.S. J. Cell Biol. 39: 16a, 1968.

Extended Production of Insulin by Isolated Rabbit Pancreatic Islets; Evidence for Biosynthesis of Insulin, Boder, G.B., Root, Mary., Chance, R.E. Johnson, I.S. Proc. Soc. Exptl. Biol. Med, 131:507–513, 1969.

Visible Light Inhibits Growth of Chinese Hamster Ovary Cells. George B. Boder, Richard J. Harley, Walter Kleinschmidt, and Daniel C. Williams. European J. Cell Biol. 31:132–136, 1983.

Long Term Monolayer Cultures of Islet Cells from Neonatal Mice. Boder, G.B., Shaw, W.N. and Smith, R.E. J. Cell Biol. 59: 29a, Nov. 1973.

(List continued on next page.)

Primary Examiner—Michael P. Woodward
Assistant Examiner—Mary K. Zeman
Attorney, Agent, or Firm—Barnes & Thornburg

[57] ABSTRACT

A tissue graft construct comprising submucosal tissue of a warm-blooded vertebrate and a proliferating population of cells is described. The submucosal graft constructs used in accordance with the present invention induce host tissue proliferation, remodeling and regeneration of appropriate tissue structures upon implantation in a host.

6 Claims, No Drawings

OTHER PUBLICATIONS

Changes in the Islets of Langerhans in the Obese Zucker Rat. Lara–Inge Larsson, George B. Boder, and Walter N. Shaw. *Lab. Invest.* 36:593–598, 1977.

Mineralization in Cultured Adult Rat Bone Cells. Evaluation by Video Time Lapes, Scanning Electron Microscopy and Energy Dispersive X–ray Analyses. D. C. Williams, D.C. Paul, C.C. Johnston, Jr., and G.B. Boder. *J. Cell Biol.* 91:22a, 1981.

Introduction to techniques in Cell Culture. George B. Boder and Robert N. Hyll. *Manual of Industrial Microbiology and Technology*, Ed. A.L. Domain and N.A. Solomon, pp. 248–261, 1986.

Large Scale Production of Monocional Antibodies in Suspension Culture. M.P. Backer, L.S. Metzger, P.L. Slaber, K.L. Nevitt, and G.B. Boder. *Biotechnology and Bioengineering* 32:993–1000, 1988.

17–$\beta$ Estradiol Inhibits IL–6 Production by Bone Marrow Stromal Cells and Osteoblasts in Vitro: A Potential Mechanism for the Antiosteoporotic Effects of Estrogens. Girasole et al., *The Journal of Clinical Investigation* 99:883–891, 1992.

Mammalian Cell Culture for Genetically Engineered Products. Boder, G.B. *Toxicologic Pathway*, vol. 17, No. 4, p. 827, 1989.

Directed Connective Tissue Remodeling Upon a Biologic Collagen Substrate. S.T. Badylak, G.B. Boder, R. Morff, G. Lentz *J. Cell Biochem*, Supplement 16F, p. 124, 1992.

Mini–Review: Islet Transplantation to Create a Bioartifical Pancreas. Antonios G. Mikos, Marla G. Papadakl, Styllanos Kouwroukoglou, Susan L. Ishang, and Robert C. Thomson, *Biotech and Bioengineering*, vol. 43, pp. 673–677(1994).

Tissue Engineering of Islet Equivalent. CY Kuo, GA Burghan, HG Herrod and TW Budd. *Biological Abstracts* A302 (1742), 1994.

Biohybrid Islet–Gland Equivalent for Transplantation. Chao–Ying, George A. Burghan, and Henry G. Herrod, *Journal of Cellular Biochemistry*, Supplement 18C, PZ110, Feb. 13–26, 1994.

Basement Membrane Complexes with Biological Activity. Hynda K. Klelnman, Mary L. McGarvey, John R. Hassell, Vicki L. Star, Frances B. Cannon, Gordon W. Laurie, and George R. Martin, *Biochemistry* 25:312–316, 1986.

Formation of Pseudioslets from Human Pancreatic Cultures, Chao Y. Kuo, Henry G. Herrod, and George A. Burghan. *Pancreas* vol. 7, No. 3, pp. 320–325, 1992.

Cultures of Animal Cells: A Manuel of Basic Technique. R. Ian Freshnay. Chapters 12 and 13, pp. 119–143, Alan R. Liss, Inc., New York, 1994.

Bioartificial Organs. Richard Skalak and Fred Fox, eds. *Tissue Engineering*, Chapter V, pp. 208–242, 1988.

5,753,267

METHOD FOR ENHANCING FUNCTIONAL PROPERTIES OF SUBMUCOSAL TISSUE GRAFT CONSTRUCTS

This is a continuation of Ser. No. 08/386,452, filed Feb. 10, 1995, and now U.S. Pat. No. 5,695,998.

FIELD OF THE INVENTION

The present invention relates to the culturing of eukaryotic cells. More particularly, this invention is directed to a method for supporting the growth and tissue differentiation of eukaryotic cells in vitro, by contacting the eukaryotic cells with submucosal tissue of a warm-blooded vertebrate, under conditions conducive to eukaryotic cell proliferation.

BACKGROUND AND SUMMARY OF THE INVENTION

Tissue culture allows the study in vitro of animal cell behavior in an investigator-controlled physiochemical environment. However, cellular morphology and metabolic activity of cultured cells are affected by the composition of the substrate on which they are grown. Presumably cultured cells function best (i.e. proliferate and perform their natural in vivo functions) when cultured on substrates that closely mimic their natural environment. Currently, studies in vitro of cellular function are limited by the availability of cell growth substrates that present the appropriate physiological environment for proliferation and development of the cultured cells.

The ability of complex substrates to support cell growth in vitro has been previously reported, and matrix products supporting such growth are commercially available. For example, Becton Dickinson currently offers two such products: Human Extracellular Matrix and MATRIGEL® Basement Membrane Matrix. Human Extracellular Matrix is a chromatographically partially purified matrix extract derived from human placenta and comprises laminin, collagen IV, and heparin sulfate proteoglycan. (Kleinman, HK et al., U.S. Pat. No. 4,829,000 (1989)) MATRIGEL® is a soluble basement membrane extract of the Engelbreth-Holm-Swarm (EHS) tumor, gelled to form a reconstituted basement membrane. Both of these matrix products require costly biochemical isolation, purification, and synthesis techniques and thus production costs are high.

The present invention is directed to the use of vertebrate submucosa-derived matrices as substrates for the growth and attachment of a wide variety of cell types. The collagenous matrices for use in accordance with the present invention comprise highly conserved collagens, glycoproteins, proteoglycans, and glycosaminoglycans in their natural configuration and natural concentration. The extracellular collagenous matrix for use in this invention is derived from submucosal tissue of a warm-blooded vertebrate. Submucosal tissue can be obtained from various sources, including intestinal tissue harvested from animals raised for meat production, including, for example, pigs, cattle and sheep or other warm-blooded vertebrates. This tissue can be used in either its natural configuration or in a comminuted or partially digested fluidized form. Vertebrate submucosal tissue is a plentiful by-product of commercial meat production operations and is thus a low cost cell growth substrate, especially when the submucosal tissue is used in its native layer sheet configuration.

The submucosal cell growth substrates of this invention provide cells with a collagenous matrix environment in vitro resembling that found in vivo. The natural composition and configuration of submucosal tissue provides a unique cell growth substrate that promotes the attachment and proliferation of cells.

Accordingly, one object of the present invention is to provide a relatively inexpensive cell culture growth substrate that promotes or induces growth and differentiation of cells cultured in vitro.

Another object of this invention is to provide a method for improving cell proliferation in cell/tissue culture by using vertebrate submucosal tissue as a substrate for cell/tissue growth in vitro.

Another object of this invention is to provide a cell culture composition including a proliferating cell population in contact with submucosal tissue of a warm-blooded vertebrate and a nutrient medium for support of the growth of said cell population.

Still a further object of this invention is to provide a model system for studying tumor cell growth. The model system comprising a proliferating tumor cell population in contact with submucosal tissue of a warm-blooded vertebrate and a nutrient medium.

It has been reported that compositions comprising submucosal tissue of the intestine of warm-blooded vertebrates can be used as tissue graft materials in sheet or fluidized form. U.S. Pat. No. 4,902,508 describes tissue graft compositions that are characterized by excellent mechanical properties, including high compliance, a high burst pressure point, and an effective porosity index. These properties allow such compositions to be used for vascular and connective tissue graft constructs. When used in such applications the preferred graft constructs serve as a matrix for the in vivo regrowth of the tissues replaced by the graft constructs. U.S. Pat. No. 5,275,826 describes use of fluidized forms of vertebrate submucosal tissues as injectable or implantable tissue grafts.

An additional object of the present invention is to enhance or expand the functional properties of vertebrate submucosal tissues as an implantable or injectable tissue graft construct by seeding the submucosal tissue in vitro with preselected or predetermined cell types prior to implanting or injecting the graft construct into the host.

DETAILED DESCRIPTION OF THE PREFERRED EMBODIMENTS

There is provided in accordance with this invention a method and composition for supporting the proliferation and inducing tissue differentiation of eukaryotic cells cultured in vitro. Generally the method comprises the step of contacting eukaryotic cells, in vitro, with a vertebrate submucosa-derived collagenous matrix under conditions conducive to eukaryotic cell growth. The term "contacting" as used herein with reference to cell culture is intended to include both direct and indirect contact, for example in fluid communication, of the submucosal tissue and the cultured cells. The term "conditions conducive to eukaryotic cell growth" as used herein refers to the environmental conditions, such as sterile technique, temperature and nutrient supply, that are considered optimal for eukaryotic cell growth under currently available cell culture procedures. Although optimum cell culture conditions used for culturing eukaryotic cells depend somewhat on the particular cell type, cell growth conditions are generally well known in the art. However a number of differentiated cell types are still considered difficult to culture (i.e. islets of Langerhans, hepatocytes, chondrocytes, osteoblasts, etc.).

The collagenous matrix component of the present cell culture substrate is derived from vertebrate submucosa and comprises naturally associated extracellular matrix proteins, glycoproteins and other factors. Preferably the collagenous matrix comprises intestinal submucosal tissue of a warm-blooded vertebrate. The small intestine of warm-blooded vertebrates is a particularly preferred source of the cell culture substrate for use in this invention.

Suitable intestinal submucosal tissue typically comprises the tunica submucosa delaminated from the tunica muscularis and at least the luminal portion of the tunica mucosa. In one preferred embodiment of the present invention the intestinal submucosal tissue comprises the tunica submucosa and basilar portions of the tunica mucosa including the lamina muscularis mucosa and the stratum compactum which layers are known to vary in thickness and in definition dependent on the source vertebrate species.

The preparation of submucosal tissue for use in accordance with this invention is described in U.S. Pat. No. 4,902,508, the disclosure of which is expressly incorporated herein by reference. A segment of vertebrate intestine, preferably harvested from porcine, ovine or bovine species, but not excluding other species, is subjected to abrasion using a longitudinal wiping motion to remove the outer layers, comprising smooth muscle tissues, and the innermost layer, i.e., the luminal portion of the tunica mucosa. The submucosal tissue is rinsed with saline and optionally sterilized; it can be stored in a hydrated or dehydrated state. Lyophilized or air dried submucosa tissue can be rehydrated and used in accordance with this invention without significant loss of its cell proliferative activity.

The graft compositions of the present invention can be sterilized using conventional sterilization techniques including glutaraldehyde tanning, formaldehyde tanning at acidic pH, propylene oxide treatment, gas plasma sterilization, gamma radiation, electron beam, peracetic acid sterilization. Sterilization techniques which do not adversely affect the mechanical strength, structure, and biotropic properties of the submucosal tissue is preferred. For instance, strong gamma radiation may cause loss of strength of the sheets of submucosal tissue. Preferred sterilization techniques include exposing the graft to peracetic acid, 1–4 Mrads gamma irradiation (more preferably 1–2.5 Mrads of gamma irradiation) or gas plasma sterilization; peracetic acid sterilization is the most preferred sterilization method. Typically, the submucosal tissue is subjected to two or more sterilization processes. After the submucosal tissue is sterilized, for example by chemical treatment, the tissue may be wrapped in a plastic or foil wrap and sterilized again using electron beam or gamma irradiation sterilization techniques.

The submucosal tissue specified for use in accordance with this invention can also be in a fluidized form. Submucosal tissue can be fluidized by comminuting the tissue and optionally subjecting it to protease digestion to form a homogenous solution. The preparation of fluidized forms of submucosa tissue is described in U.S. Pat. No. 5,275,826, the disclosure of which is expressly incorporated herein by reference. Fluidized forms of submucosal tissue are prepared by comminuting submucosa tissue by tearing, cutting, grinding, or shearing the harvested submucosal tissue. Thus pieces of submucosal tissue can be comminuted by shearing in a high speed blender, or by grinding the submucosa in a frozen or freeze-dried state to produce a powder that can thereafter be hydrated with water or a buffered saline to form a submucosal fluid of liquid, gel or paste-like consistency. The fluidized submucosa formulation can further be treated with a protease such as trypsin or pepsin at an acidic pH for a period of time sufficient to solubilize all or a major portion of the submucosal tissue components and optionally filtered to provide a homogenous solution of partially solubilized submucosa.

The viscosity of fluidized submucosa for use in accordance with this invention can be manipulated by controlling the concentration of the submucosa component and the degree of hydration. The viscosity can be adjusted to a range of about 2 to about 300,000 cps at 25° C. Higher viscosity formulations, for example, gels, can be prepared from the submucosa digest solutions by adjusting the pH of such solutions to about 6.0 to about 7.0.

Applicants have discovered that compositions comprising submucosal tissue can be used for supporting growth or proliferation of eukaryotic cells in vitro. Submucosal tissue can be used in accordance with this invention as a cell growth substrate in a variety of forms, including its native sheet-like configuration, as a gel matrix, as an addition for art-recognized cell/tissue culture media, or as coating for culture-ware to provide a more physiologically relevant substrate that supports and enhances the proliferation of cells in contact with the submucosal matrix. The submucosal tissue provides surfaces for cell adhesion and also induces cell differentiation. The submucosal tissue is preferably sterilized prior to use in cell culture applications, however nonsterile submucosal tissue can be used if antibiotics are included in the cell culture system.

In one preferred embodiment cells are seeded directly onto sheets of vertebrate submucosal tissue under conditions conducive to eukaryotic cell proliferation. The porous nature of submucosal tissue allows diffusion of cell nutrients throughout the submucosal matrix. Thus, for example, cells can be cultured on either the luminal or abluminal surface of the submucosal tissue. The luminal surface is the submucosal surface facing the lumen of the organ source and typically adjacent to an inner mucosa layer in vivo whereas the abluminal surface is the submucosal surface facing away from the lumen of the organ and typically in contact with smooth muscle tissue in vivo.

Cells cultured on solid sheets of vertebrate submucosal tissue display a different growth pattern, and exhibit different interactions with the submucosal growth substrate, depending on which side of the submucosal sheet the cells are grown. Histological examination of tissue/cells cultured on intestinal submucosal tissue sheets in accordance with this invention reveals that cells that are seeded onto the abluminal surface not only grow/proliferate along the surface of the submucosal tissue, but they also more readily migrate into and proliferate within the submucosal tissue itself. The luminal surface comprises a more dense matrix than the abluminal side and thus cells are less likely to penetrate the luminal side. Cells that are seeded onto the luminal surface attach to the matrix but generally do not penetrate the surface. However certain cell types are capable of penetrating both the abluminal and luminal surfaces (eg squamous carcinoma cells and fibroblasts). In addition, certain cell types, such as fetal rat cells, when seeded on the luminal side proliferate to form a polylayer of cells. Cells of this polylayer can differentiate to perform functions characteristic of cells in vivo and indicative of their position in the polylayer.

In one embodiment in accordance with the present invention the submucosal cell substrates can be utilized to provide a model system for studying tumor cell growth. Tumor invasion of basement membranes is a crucial step in the complex multistage process which leads to the formation of metastases. Common features of the invasive process include: (a) attachment of the tumor cells to the basement membrane via cell surface receptors; (b) secretion of enzymes by the tumor cells that cause degradation of the adjacent extracellular matrix (ECM) structures; and (c) migration of the cells through the matrix components. Tumor cells cultured in vitro however, typically form a monolayer or polylayer of flattened cells that is not appropriate for studying the process of tissue invasion by tumor cells.

Cell culture substrates comprising submucosal tissue of warm blooded vertebrates can be used to culture various tumor cells types in vitro as a model of tumor cell growth characteristics. Such a model system would allow investigation of the molecular mechanisms involved in tumor invasion and could ultimately lead to the development of novel anti-metastatic therapeutic strategies. In particular, such a model system would enable the analysis in vitro of the effect of various compounds, such as growth factors, anti-tumor agents, chemotherapeutics, antibodies, irradiation or other factors known to effect cell growth, on the growth characteristics of tumor cells.

To analyzing in vitro the effect of varying cell growth conditions on the growth characteristics of tumor cells, the tumor cells are seeded on a cell growth substrate comprising submucosal tissue of a warm-blooded vertebrate and provided a culture medium containing nutrients necessary to the proliferation of said cells. The seeded cells are then cultured under a preselected variable cell growth condition for varying lengths of time and then the mucosal tissue substrate and the tumor cell population on the substrate are histologically examined. The selected growth condition can be the presence or concentration of a tumor cell growth modifier compound, such as cytokines or cytotoxic agents, in the nutrient medium. Alternatively the selected growth condition may be the modification of environmental factors such as temperature, pH, electromagnetic radiation, or nutrient composition. The effect of the selected growth condition on the morphology and growth of tumor cells can then be assessed by histological analysis of control (tumor cells cultured in the absence of the selected growth condition) and test tumor cell cultures.

Both the fluidized and sheet forms of submucosal tissue can be used to develop tumor cell invasion model systems. For example, the fluidized form can be used to coat polycarbonate filters and then applied to a Boyden chamber-like device. Various stains, fluorescent markers, or radionucleotides can be used to obtain quantitative as well as qualitative invasion data. In addition, submucosal tissue can be used to assess the invasive potential of various cell types as well as a means for selective isolation of cells based upon their invasive potential.

In another embodiment of the present invention, cell growth substrates in accordance with the present invention are formed from fluidized forms of submucosal tissue. The fluidized submucosal tissue can be gelled to form a solid or semi-solid matrix. Eukaryotic cells can then be seeded directly on the surface of the matrix and cultured under conditions conducive to eukaryotic cell proliferation.

The cell growth substrate of the present invention can be combined with nutrients, including minerals, amino acids, sugars, peptides, proteins, or glycoproteins that facilitate cellular proliferation, such as laminin and fibronectin and growth factors such as epidermal growth factor, platelet-derived growth factor, transforming growth factor beta, or fibroblast growth factor. In one preferred embodiment fluidized or powder forms of submucosal tissue can be used to supplement standard eukaryotic culture media to enhance the standard media's capacity for sustaining and inducing the proliferation of cells cultured in vitro.

In accordance with the present invention there is provided a cell culture composition for supporting growth in vitro of an eukaryotic cell population in combination with submucosal tissue of a warm-blooded vertebrate. The composition comprises nutrients, and optionally growth factors required for optimal growth of the cultured cells. The submucosa substrates of the present invention can be used with commercially available cell culture liquid media (both serum based and serum free). When grown in accordance with this invention, proliferating cells can either be in direct contact with the submucosal tissue or they can simply be in fluid communication with the submucosal tissue. It is anticipated that the cell growth compositions of the present invention can be used to stimulate proliferation of undifferentiated stems cells as well as differentiated cells such as islets of Langerhans, hepatocytes and chondrocytes. Furthermore the described cell growth composition is believed to support the growth of differentiated cells while maintaining the differentiated state of such cells.

It has been well documented that submucosal tissue is capable of inducing host tissue proliferation, remodeling and regeneration of appropriate tissue structures upon implantation in a number of microenvironments in vivo (e.g., tendon, ligament, bone, articular cartilage, artery, and vein). The use of such tissue in sheet form and fluidized forms for inducing the formation of endogenous tissues is described and claimed in U.S. Pat. Nos. 5,281,422 and 5,275,826, the disclosures of which are expressly incorporated by reference.

In one embodiment of the present invention the tissue replacement capabilities of graft compositions comprising submucosal tissue of warm-blooded vertebrates are further enhanced or expanded by seeding the tissue with various cell types, prior to implantation. For example, submucosal tissue may be seeded with endothelial cells, keratinocytes, or islet of langerhans cells for use as a vascular graft, skin replacement, or auxiliary pancreas, respectively. Alternatively, the submucosal tissue can be seeded with mesenchymal cells (stem cells) initially for expansion of the cell population and thereafter for implantation into a host. Submucosal tissue can also serve as a delivery vehicle for introducing genetically modified cells to a specific location in a host. The submucosal tissue for use in accordance with this embodiment can either be in a fluidized form or in its native solid form. Optionally, after the submucosal tissue has been seeded with eukaryotic cells, the graft composition can be subjected to conditions conducive to the proliferation of eukaryotic cells to further expand the population of the seeded cells prior to implantation of the graft into the host.

In one embodiment, compositions comprising submucosal tissue and a proliferating cell population can be encapsulated in a biocompatible matrix for implantation into a host. The encapsulating matrix can be configured to allow the diffusion of nutrients to the encapsulated cells while allowing the products of the encapsulated cells to diffuse from the encapsulated cells to the host cells. Suitable biocompatible polymers for encapsulating living cells are known to those skilled in the art. For example a polylysine/ alginate encapsulation process has been previously described by F. Lim and A. Sun (Science Vol. 210 pp. 908–910). Indeed, vertebrate submucosa itself could be used advantageously to encapsulate a proliferating cell population on a submucosal matrix in accordance with this invention for implantation as an artificial organ.

Submucosal tissue advantageously provides a physiological environment that supports the differentiation of cells cultured in vitro on the submucosal tissue. Thus, cell culture substrates comprising submucosal tissue can be used in combination with standard cell culture techniques known to those of ordinary skill in the art, to produce tissue grafts, in vitro, for implantation into a host in need thereof. The cells of such a tissue perform their proper natural function based on cell type and position within the submucosal tissue graft construct.

The method of forming a tissue graft in vitro comprises the steps of seeding eukaryotic cells onto a cell growth substrate comprising submucosal tissue of a warm-blooded vertebrate and culturing the cells in vitro under conditions conducive to proliferation of the eukaryotic cells. Advantageously the synthesis in vitro of a tissue graft construct, wherein the cells of the tissue perform their proper natural function, allows the generation of tissue grafts from an initially small cell population that can be expanded in vitro prior to implantation.

EXAMPLE 1

Sterilization of Submucosal Tissue

Because cell culture techniques must be performed under strict aseptic conditions, if antibiotics are not included in the culture system, the submucosa tissue must be prepared in a sterile manner for use as a cell culture substrate. Numerous sterilization methods have been investigated to assess the effect of sterilization on the biotropic properties of submucosal tissue. Sterilization techniques which do not significantly weaken the mechanical strength and biotropic properties of the tissue are preferred. The following sterilization methods for intestinal submucosa have been evaluated: peracetic acid sterilization, 2.5 Mrad gamma-irradiation, 1.0 Mrad gamma-irradiation, Exspor (Alcide, Norfolk, Conn.) sterilization and various combinations of these sterilization methods. Gamma-irradiation was performed on hydrated submucosal tissue using a $^{60}$Cobalt-gamma chamber. Exspor sterilization was performed according to manufacturer's specifications using a sterilant volume (ml) to intestinal submucosa (g) ratio of 10 to 1.

Various cell types (e.g., IMR-90, FR, HT-29, RPEC) were seeded upon the sterilized submucosa and their growth characteristics were analyzed at 1,3,7 and 14 days. Results obtained for all cell types showed that submucosal derived growth substrates sterilized by gamma-irradiation or peracetic acid treatments supported some degree of adherence and growth of cells. However, cells seeded onto peracetic acid sterilized submucosal derived substrates showed increased adherence, increased survival, and enhanced rates of proliferation and differentiation; peracetic acid appears to be the preferred sterilization technique for preparation of submucosa as a cell culture substrate.

EXAMPLE 2

Sterilization of Submucosal Tissue with Peracetic Acid

Submucosal tissue is soaked in a peracetic acid/ethanol solution for 2 hours at room temperature using a ratio of 10:1 (mls peracetic solution: grams submucosal tissue) or greater. The peracetic acid/ethanol solution comprises 4% ethanol, 0.1% (volume: volume) peracetic acid and the remainder water. The 0.1% peracetic acid component is a dilution of a 35% peracetic acid stock solution commercially available and defined as in table 1. Preferably, the submucosal tissue is shaken on a rotator while soaking in the peracetic acid solution. After two hours, the peracetic acid solution is poured off and replaced with an equivalent amount of lactated Ringer's solution or phosphate buffered saline (PBS) and soaked (with shaking) for 15 minutes. The submucosal tissue is subjected to four more cycles of washing with lactated Ringer's or PBS and then rinsed with sterile water for an additional 15 minutes.

TABLE 1

Chemical Composition of the 35% Peracetic Acid Solution

| Composition, % by weight | |
|---|---|
| Peracetic acid | 35.5 |
| Hydrogen peroxide | 6.8 |
| Acetic acid | 39.3 |
| Sulfuric acid | 1.0 |
| Water | 17.4 |
| Acetyl peroxide | 0.0 |
| Stabilizer | 500 PPM |
| Typical active oxygen analysis, % by weight | |
| Active Oxygen as peracid | 7.47 |
| Active Oxygen as $H_2O_2$ | 2.40 |
| Total active oxygen | 10.67 |

EXAMPLE 3

Growth Characteristics Of Various Cell Types On Sterilized Submucosa

Small intestinal submucosa was harvested and prepared from freshly euthanatized pigs as described in U.S. Pat. No. 4,902,508. Following sterilization via various techniques (gamma irradiation, peracetic acid, etc.), the submucosal tissue was clamped within a polypropylene frame to create a flat surface area (50 mm$^2$) for cell growth. The frame was submerged in culture medium to allow access of medium nutrients to both surfaces of the submucosal tissue. Various cell types were seeded ($3\times10^4$ cells/submucosal tissue section) on the submucosal tissue and then placed in a 5% $CO_2$, 95% air incubator at 37° C. Following various periods of time, the seeded submucosal tissue was fixed in 10% neutral buffered formalin, embedded in paraffin, and sectioned (6 um). Various histological and immunohistochemical staining procedures were then applied to determine the cell growth characteristics.

To date, the growth characteristics of the following cell lines have been studied using submucosal tissue as a growth substrate:

| CELL LINE | CELL LINE DESCRIPTION |
|---|---|
| CHO | Chinese hamster ovary cells |
| 3T3 | Swiss albino mouse embryo fibroblasts |
| C3H10T1/2 | C3H mouse embryo, multi-potential |
| FR | Fetal rat skin (Sprague Dawley) |
| IMR90 | Human fetal lung fibroblasts |
| HT-29 | Human colon adenocarcinoma, moderately well differentiated, grade II |
| RPEC | Rat pulmonary endothelial cells |
| HUVEC | Human umbilical vein cells |
| SCC-12 | Squamous Cell Carcinoma |

Table 2 summarizes various cell types and the corresponding specific medium conditions used to culture on the submucosa derived cell culture substrates. The medium chosen represents optimal or near optimal conditions for propagation of each cell type under standard cell culture conditions (i.e., plastic tissue culture flasks). All cell preparations were incubated at 37° C. in a humidified atmosphere of 5% $CO_2$/air.

TABLE 2

Cell types and corresponding culture conditions investigated using Intestinal Submucosal Tissue as a cell growth matrix

| CELL TYPE | MEDIUM |
| --- | --- |
| 3T3 (American Type Culture Collection (ATCC), CRL 1658) Swiss mouse embryo fibroblasts | DMEM (Dulbecco's modified Eagle's medium) with 1.5 g/L $NaHCO_3$, 10% NNCS (neonatal calf serum), 100 U/ml penicillin, 100 ug/ml streptomycin, 2 mM L-glutamine |
| FR (ATCC, CRL 1213) cell line developed from a skin biopsy of a fetal (18 day gestation) germ-free Sprague Dawley rate | DMEM, 10% NNCS, 100 U/ml penicillin, 100 ug/ml streptomycin, 2 mM L-glutamine |
| HT-29 (ATCC, HTB 38) cell line derived from human colon adenocarcinoma | McCoy's, 10% NNCS, 100 U/ml penicillin, 100 ug/ml streptomycin, 2 mM L-glutamine |
| HUV-EC-C (ATCC, CRL 1730) endothelial cell line isolated from human umbilical vein | F12 K medium, 10% FBS (fetal bovine serum), 100 ug/ml heparin, 50 ug/ml endothelial cell growth supplement, 100 U/ml penicillin, 100 ug/ml streptomycin, 2 mM L-glutamine |
| IMR-90 (ATCC, CCL 186) human diploid fibroblasts | McCoy's 5A medium, 20% NNCS, 100 U/ml penicillin, 100 ug/ml streptomycin, 2 mM L-glutamine |
| RPEC (J. P. Robinson, Purdue University) endothelial cell line derived from rat pulmonary endothelial cells | RPMI 1640, 5% NCS (newborn calf serum) 5% FBS (fetal bovine serum), 100 U/ml penicillin, 100 ug/ml streptomycin, 2 mM L-glutamine |
| C3H10T1/2 (ATCC, CCL 226) mouse embryo fibroblasts | BME (basal medium Eagle), 10% FBS, 100 U/ml penicillin, 100 ug/ml streptomycin, 2 mM L-glutamin |
| SCC-12 (W. Greenlee, Purdue University) squamous cell carcinoma | DMEM, 5% FBS (fetal bovine serum), 4 mM L-glutamine, 1 mM sodium pyruvate |
| CHO (Chinese Hamster Ovary Cells) | F12 Medium 10% FBS with antibiotics (Neomycin) |

The cellular growth on both the luminal and abluminal sides of intestinal submucosal tissue has been investigated. Intestinal submucosal tissue as a growth substrate exhibits sidedness; that is, the cell/matrix interactions are different when the cells are cultured on the abluminal versus the luminal side of the intestinal submucosal tissue. When selected cell types, such as rat FR cells are seeded on the luminal side, the cells attach to the matrix surface and proliferate to form a cellular polylayer. Alternatively, when FR cells are seeded on the abluminal side, the cells not only grow along the surface but also migrate into the submucosal matrix.

The stratum compactum of the luminal side of vertebrate intestinal submucosal tissue provides a dense connective tissue matrix and more readily supports monolayer or polylayer formation of select cell types (i.e. endothelial and epithelial cells). Alternatively, the abluminal side represents a more loose connective tissue structure that more readily supports migration of cells within the matrix structure (i.e. fibroblasts).

IMR-90 fibroblasts, when seeded upon the abluminal or luminal sides of the intestinal submucosal tissue, quickly became adherent and proliferated throughout the matrix components. These cells illustrated their characteristic spindle shape and large vesicular nucleus within the extracellular matrix components. However, 3T3 fibroblasts showed minimal adherence and growth potential when seeded upon the intestinal submucosal tissue.

Endothelial cells formed a confluent monolayer of spindle-shaped cells along the stratum compactum surface of the intestinal submucosal tissue within 3 days. At later times the monolayer became more dense and some cells intercalated down into the matrix components. Interestingly, some endothelial cells that penetrated into the matrix components formed a lining along the lumen of structures representing original blood vessels of the native intestine.

To date, the growth characteristics of the following primary cell strains have been studied using intestinal submucosal tissue as a growth substrate:

CELL STRAIN

Rat Cardiac Muscle

Porcine Smooth Muscle (aorta)

Porcine Endothelial (aorta)

Rabbit Smooth Muscle (aorta)

Rabbit Endothelial(aorta)

Porcine Smooth Muscle and Endothelial (mixed & co-cultured)

Human Osteoblasts

Human Endothelial Cells

Primary cell strains are cells that have been harvested from an organism and placed in culture. Subsequent passages of these cells (from 2–3 times) using standard in vitro cell culture techniques (to increase the number of cells) were frozen for later use. Each of the above listed cell strains was thawed, cultured in the presence of intestinal submucosal tissue and examined histologically. Each of the cultured cell strain populations proliferated and retained their differentiated appearance as determined by histological examination. For example, after 7–14 days of culture on intestinal submucosal tissue: the human osteoblast cells continued to accumulate appatite crystals and respond to osteogenic stimuli such as hormones; rat cardiac muscle cells retained their contractile properties; porcine smooth muscle cells retained smooth muscle actin; and porcine endothelial cells made factor eight.

EXAMPLE 4

Intestinal Submucosal Cell Culture Substrates as a Tumor Cell Growth Model System The morphology and invasive properties of an established cell line from a human squamous cell carcinoma of the face known as SCC-12 (obtained from W. Greenlee, Purdue University) cultured in vitro were studied. When grown under standard cell culture conditions for skin cells (e.g., gamma-irradiated or mitomycin C-treated feeder layer of Swiss 3T3 mouse fibroblasts) a monolayer of flattened cells is formed. However SCC-12 cells when seeded upon the abluminal surface of intestinal submucosal tissue, showed, upon histological examination active degradation of the submucosal matrix components and invasion of the intestinal submucosal tissue.

SCC-12 cells were seeded ($3 \times 10^4$ cells/0.8 $cm^2$ of intestinal submucosal tissue) on either the abluminal or luminal surface of sterilized intestinal submucosal tissue and floated in growth medium consisting of DMEM containing 5% fetal calf serum, 4 mM L-glutamine, and 1 mM sodium pyruvate. At timepoints representing 3, 7, 14, and 21 days, the growth characteristics were analyzed using standard histologic techniques. On day 3, the cells were strongly adherent and appeared to form a continuous layer (1–2 cells thick) along surface of the intestinal submucosal tissue. Morphologically, the cells were round and actively producing extracellular matrix products. After 7 days, a significant difference was noted in the cells ability to invade the abluminal versus the luminal surface of the intestinal submucosal tissue. The layer of cells along the luminal surface of the intestinal submucosal tissue appeared to only increase in density. Alternatively, those cells seeded upon the abluminal surface, showed active degradation of the submucosal matrix components and penetration up to 30 um. At longer durations, there was an increasing number of cells at greater depths of penetration and a greater extent of intestinal submucosal tissue degradation. Although the SCC-12 cells actively invade intestinal submucosal tissue from both the abluminal and luminal surfaces, the observed invasion rate was greater when SCC-12 cells were placed on the abluminal side.

EXAMPLE 5

Intestinal Submucosal Tissue Supports Cytodifferentiation

FR Epithelial cells form a stratified polylayer when cultured on the luminal (stratum compactum) side of intestinal submucosal tissue. Cells adjacent to the intestinal submucosal tissue were columnar in shape and became progressively more flattened near the surface of the polylayer. After 14 days, structures resembling desmosomes were identified and the cellular layer stained positively for cytokeratin with a pan cytokeratin antibody. In addition, it appeared that the epithelial cells produced supporting matrix products (potentially basement membrane) as they do in vivo under normal healthy conditions. These findings suggest that the intestinal submucosal tissue supports natural epithelial cell maturation and differentiation processes.

The observed stratification of FR cells grown on the luminal side (stratum compactum) of a submucosal growth substrate provides evidence that the intestinal submucosal tissue supports and induces cellular differentiation in vitro. To verify the induction of cytodifferentiation of the FR cells, immunohistochemical and immunofluorescence analyses were performed for detecting the production of cytokeratin by FR cells cultured in the presence and absence of intestinal submucosal tissue. Cytokeratin is a predominant intracellular structural protein produced by terminally differentiated epithelial cells known as keratinocytes. Immunohistochemistry was performed on the protease-digested, formalin-fixed, paraffin embedded sections of FR cells grown on intestinal submucosal tissue using an anti-pan cytokeratin (C2931, Sigma, St. Louis, Mo.) as the primary antibody. Immunodetection was performed using the avidin-biotin complex (ABC) method and the Biogenex supersensitive StriAviGen kit (Vector Laboratories, Burlingame, Calif.). Tissue sections representing rat skin biopsies and HT29 cells grown on intestinal submucosal tissue were included in the analysis as positive and negative controls, respectively.

Results indicated a gradation of cytokeratin staining along the FR cellular polylayer with those cells at the surface of the polylayer staining most intensely. A similar positive staining pattern was observed in the cells forming the epidermal layer of the rat skin. However, no cytokeratin was detected in the specimens representing HT29 cells cultured on intestinal submucosal tissue.

An immunofluorescence analysis for cytokeratin was performed using flow cytometry to determine if the FR cell line expressed the differentiation product cytokeratin under standard culture conditions (in the absence of intestinal submucosal tissue). Swiss 3T3 Fibroblast (3T3) and squamous cell carcinoma (SCC-12) cell lines were included in the analysis as negative and positive controls respectively. Cells were harvested from tissue culture flasks, permeabilized using a cold methanol pretreatment, and incubated in the presences of anti-pan cytokeratin antibody at various dilutions (including the absence of anti-pan cytokeritin antibody to serve as a control). A goat anti-mouse antibody conjugated with fluorescein isothiocyanate (GAM-FITC) was then applied to facilitate immunodetection. The cell preparations were then analyzed on a EPICS Elite flow cytometer (Coulter Corp., Hialeah, Fla.) using 488 nm excitation produced by an air-cooled argon laser. Fluorescence emissions were measured at 525 nm with a bandpass filter. Untreated cells and cells treated only with GAM-FITC were also analyzed to establish background fluorescence levels. Table 3 represents the relative percentage of FITC fluorescence for each cell type following indirect immunofluorescence staining. As the data indicate only the positive control SCC-12 cell line expresses cytokeratin and the FR cell line does not express cytokeratin under standard culture conditions in the absence of submucosal substrate.

TABLE 3

Indirect Immunofluorescence Analysis for Cytokeratin BCC-12, 3T3 and FR Cells

| Cell Type | Dilution of Anti-Pan Cytokeratin | Percent GAM-FITC Fluorescence |
| --- | --- | --- |
| SCC-12 | 0 (control) | 2% |
| SCC-12 | 1:100 | 72% |
| SCC-12 | 1:400 | 74% |
| SCC-12 | 1:1000 | 76% |
| SCC-12 | 1:4000 | 72% |
| 3T3 | 0 (control) | 11% |
| 3T3 | 1:100 | 10% |
| 3T3 | 1:400 | 18% |
| 3T3 | 1:1000 | 8% |
| 3T3 | 1:4000 | 5% |
| FR | 0 (control) | 6% |
| FR | 1:100 | 11% |
| FR | 1:400 | 6% |
| FR | 1:1000 | 4% |
| FR | 1:4000 | 4% |

EXAMPLE 6

Isolation Of Hamster Pancreatic Islets

Hamster pancreatic islets were isolated as previously described by Gotoh et al. (*Transportation* Vol. 43, pp. 725–730(1987)). Briefly, 6–8 week old Golden hamsters (Harlan, Indianapolis, Ind.) were anesthetized via inhalation of Metofane (Methoxyflurane; Pitman-Moore; Mundelein, Ill.). The common bile duct was cannulated under a stereomicroscope with a polyethylene catheter (PE-10 tubing; CMS; Houston, Tex.), through which approximately 3–4 mls of ice cold M-199 medium (commercially available from Gibco BRL) containing 0.7 mg/ml of collagenase P was injected slowly until whole pancreas was swollen. The pancreas was excised and digested at 37° C. for approximately 50 minutes in M-199 medium containing 100 µg/ml of penicillin G and 100 µg/ml of streptomycin (no additional collagenase). The digest was washed three times in ice cold M-199 medium and passed sequentially through a sterile 500 µm stainless steel mesh, then a 100 µm mesh. Following purification by centrifugation through a ficoll density gradient (1.045, 1.075, 1.085 and 1.100) at 800 g for 10 min, islets were recovered from the top two interfaces.

Culturing of Pancreatic Islet Cells on Intestinal Submucosal Tissue

Islets of Langerhans (islet cells) were cultured on submucosal cell growth substrates at 37° C. in an incubator supplemented with 5% CO and 95% air. The islet cells were cultured in the presence of various forms of intestinal submucosal tissue using the following procedures:

1. Direct Contact: Intestinal submucosal tissue and the cultured cells physically contact one another.
2. Indirect Contact: Intestinal submucosal tissue and the cultured cells are separated by a stainless steel mesh.
3. Solubilized intestinal submucosal tissue is added to the culture media
4. Cells are cultured on solubilized intestinal submucosa coated culture plate. The coating was applied by placing 1 ml of solubilized intestinal submucosal tissue in a 35 mm culture plate, heated at 37° C. for 2 hours, removing the excess intestinal submucosal tissue fluid by aspiration and washing the coated plates once with culture media.

In direct contact culture method, an intestinal submucosa membrane of approximately 1×1 cm was placed on top of stainless steel mesh with the stratum compactum side facing up. Isolated islets were then placed onto the membrane and continuously cultured in M-199 medium (commercially available from Gibco BRL) for 7 days. Cell proliferation was examined every second day under a stereomicroscope and was compared with the control group (cultured in the absence of submucosa tissue).

Sterilization of Submucosal Tissue Before Co-culturing

1. Intestinal submucosal tissue derived cell culture substrates were sterilized by several different means: peracetic acid treatment or gamma irradiation. Gamma irradiated and the native (no further treatment after isolation of the intestinal submucosal tissue) membranes can be used directly as cell culture substrates provided they have been sufficiently rehydrated with the culture media prior to the co-culture (native membranes must be cultured in the presence of antibiotics). Peracetic acid sterilized membranes, must first be washed to remove residual peracetic acid prior to culturing since peracetic acid residue may be toxic to the cells. Typically peracetic acid sterilized tissues were soaked in a large quality of medium for 24 hours followed by extensive washing with the same medium.

2. Solubilized forms of intestinal submucosal tissue were sterilized by dialyzing against 6.5% chloroform in either 0.1M acetic acid (AA-submucosa) or phosphate buffered saline (PBS-submucosa) for 2 hours at room temperature. The exterior surface of the dialysis tubing is sterilized by rinsing the outside of the tubing with 70% alcohol prior to removal of the intestinal submucosal tissue. The dialysis tubing has a molecular weight cut-off of 12,000–14,000; thus, proteins retained inside tubing are those with molecular weight greater than 14,000.

Results

In the control group (islets cultured in the absence of submucosa tissue) examination of seven day cultures revealed that fibroblast cells had overgrown the islet cells.

When islet cells were cultured on growth substrates comprising intestinal submucosal tissue, overgrowth of the islet cells by fibroblast cells did not occur. In intestinal submucosal tissue direct culture systems, the islets became loosely packed with many cells surrounding the islet capsule. Cells migrated from the capsule and cell proliferation occurred on top of the membrane in the absence of fibroblast overgrowth. Culturing islet cells on intestinal submucosal tissue coated culture ware also appeared to facilitate migration of epithelioid cells out of the islet capsule. Further attachment to the coating surface and the formation of a monolayer of epithelioid cells was observed.

These data indicate that submucosal substrates can be used to stimulate growth of islet cells in vitro without overgrowth of fibroblast cells. Islet cells can thus be isolated from pancreatic tissue and grown in vitro in contact with a cell growth substrate comprising intestinal submucosal tissue of a warm-blooded vertebrate under conditions conducive to the proliferation of the islet cells and without concurrent growth of fibroblasts. These islet cell culture compositions remain substantially free of fibroblast overgrowth.

We claim:

1. A method for enhancing the capabilities of a submucosal tissue graft construct to repair damaged or diseased tissue, said method comprising the step of seeding the submucosal tissue with cells selected from the group consisting of endothelial cells, keratinocytes and mesenchymal cells prior to implanting or injecting the graft construct into a host.

2. The method of claim 1 further comprising the step of subjecting the seeded graft construct to conditions conducive to the proliferation of the cells prior to implanting or injecting the graft material into the host.

3. The method of claim 1 wherein the submucosal tissue comprises tunica submucosa delaminated from both the tunica muscularis and at least the luminal portion of the tunica mucosa of vertebrate intestinal tissue.

4. The method of claim 1 wherein the cells have been genetically modified.

5. The method of claim 1, wherein the submucosal tissue is fluidized submucosal tissue.

6. The method of claim 5, wherein the fluidized submucosal tissue comprises submucosal tissue digested with an enzyme for a period of time sufficient to solubilize the tissue.

* * * * *